United States Patent
Khitrik (10) Patent No.: US 12,048,788 B1
(45) Date of Patent: Jul. 30, 2024

(54) APPARATUS AND METHOD FOR AIR TREATMENT

(71) Applicant: TADIRAN CONSUMER AND TECHNOLOGY PRODUCTS LTD., Petach Tikva (IL)

(72) Inventor: Maria Khitrik, Petach Tikva (IL)

(73) Assignee: TADIRAN CONSUMER AND TECHNOLOGY PRODUCTS LTD., Petach Tikva (IL)

(*) Notice: Subject to any disclaimer, the term of this patent is extended or adjusted under 35 U.S.C. 154(b) by 0 days.

(21) Appl. No.: 18/218,695

(22) Filed: Jul. 6, 2023

(30) Foreign Application Priority Data

Mar. 13, 2023 (IL) .......................................... 301347

(51) Int. Cl.
- *A61L 9/22* (2006.01)
- *B01D 53/32* (2006.01)
- *F24F 8/192* (2021.01)

(52) U.S. Cl.
CPC ................ *A61L 9/22* (2013.01); *B01D 53/32* (2013.01); *F24F 8/194* (2021.01); *B01D 2257/91* (2013.01); *B01D 2259/818* (2013.01)

(58) Field of Classification Search
CPC ....................................................... A61L 9/22
See application file for complete search history.

(56) References Cited

U.S. PATENT DOCUMENTS

| | | | |
|---|---|---|---|
| 2007/0245898 A1 | 10/2007 | Naito et al. | |
| 2013/0165036 A1 | 6/2013 | Kudo et al. | |
| 2022/0266315 A1 | 8/2022 | Wettels et al. | |
| 2023/0001427 A1* | 1/2023 | Kim | B03C 3/41 |
| 2023/0151984 A1* | 5/2023 | Sung | B03C 3/82 |
| | | | 96/62 |

FOREIGN PATENT DOCUMENTS

| | | | | |
|---|---|---|---|---|
| CN | 109127136 A | | 1/2019 | |
| KR | 20040100397 A | * | 12/2004 | ............... A61L 9/22 |
| WO | 2006005648 A1 | | 1/2006 | |

OTHER PUBLICATIONS

English Translation of Document ID No. KR 20040100397 A provided by the European Patent Office website espacenet.com: Choi Ha Seop; Anion Air Purifier Capable of Maximizing Anion Generation, Facilitation Air-Circulation, and Constructing Home Network; Dec. 2, 2024 (Year: 2004).*

* cited by examiner

*Primary Examiner* — Kevin Joyner
(74) *Attorney, Agent, or Firm* — Dorsey & Whitney LLP (57) ABSTRACT

There is provided apparatuses and methods for air treatment. Airflow is conveyed between an air inlet and an opposite air outlet, determining an airflow direction. A corona discharge zone or plasma zone is created across the airflow between a screen forming a first electrode and a second electrode, the screen defining a screen surface. Dust accumulation is disrupted on the screen surface using a plurality of single or multiple shaped elements defined by the screen surface.

19 Claims, 7 Drawing Sheets

APPARATUS AND METHOD FOR AIR TREATMENT

TECHNOLOGICAL FIELD

The present disclosure generally relates to apparatuses and methods for air treatment, and more particularly relates to apparatuses and methods for air treatment using corona discharges.

BACKGROUND

Air can be treated in a variety of different ways to tailor its composition for a particular use. For example, air can be purified to remove pathogens such as fungi (like Blue Mold), bacteria (*Streptococcus* A) and viruses such as *Influenza* virus and coronaviruses. Air treatment apparatuses and methods may be used in the home or in commercial properties, for example, in combination with/part of air conditioning units or as standalone devices.

Purification of air generally falls into two categories: filtration and chemical neutralization. In the category of chemical neutralization, corona discharge purifiers work by passing the air through a corona discharge—a current (electrical discharge) that passes through the air, driven by high voltage difference between electrodes. The electrical discharge creates reactive agents (molecules, radicals and ions) that chemically or physically attack and deactivate different pathogens. The current itself might also neutralize the pathogens.

Corona discharge air purifiers are broadly categorized into unipolar and bipolar. Unipolar corona discharge air purifiers include only one ionizing electrode, whereas in bipolar corona discharge air purifiers, both electrodes are ionizing and are kept at a potential difference relative to the ground.

Various purifying devices have been developed based on the corona discharge process or cold plasma/plasma phenomenon, such as ozone generators, unipolar or bipolar ion generators, hydrogen peroxide ($H_2O_2$) generators, and electrostatic filters.

However, in many of these devices which pass the electrical current through the air, the electrodes may become contaminated with dust over time, reducing the efficacy of the device. The dust may form an insulating layer on the electrodes which may block the strength of the electric field, decline the conductive surface of the electrodes and, as a result—reduce the intensity of corona discharge/plasma current that causes the reduction in the efficiency of air treatment.

Accordingly, it is desirable to provide apparatuses and methods for air treatment with improved efficacy and increased lifetimes. Furthermore, other desirable features and characteristics of the present disclosure will become apparent from the subsequent detailed description and the appended claims, taken in conjunction with the accompanying drawings and the foregoing technical field and background.

GENERAL DESCRIPTION

In an aspect, there is provided an air treatment apparatus. The air treatment apparatus comprises a hollow housing for conveying an airflow between an air inlet and an opposite air outlet, determining an airflow direction. The air treatment apparatus comprises a screen forming a first electrode, the screen being mounted in the housing between the air inlet and the air outlet and defining a screen surface. The air treatment apparatus comprises a second electrode. The air treatment apparatus is configured to apply a voltage across the first electrode and the second electrode such that a corona discharge zone is formed across the airflow between the screen and the second electrode. The screen surface is exposed to the corona discharge zone and defines one or a plurality of shaped elements. The shaped elements may be configured to disrupt dust accumulation on the screen surface.

In embodiments, each (or at least some) of the shaped elements is configured to at least partially shelter a respective downstream side portion of the screen surface from the airflow. In other words, the shaped elements may form a leeside with respect to the airflow.

In embodiments, each (or at least some) of the shaped elements is configured such that an electric field strength around the shaped element is stronger than the electric field strength in other areas of the screen surface. In other words, the shaped elements may be configured to locally focus the electric field i.e. to create local peaks of electric field strength.

In embodiments, the screen surface defines a generally smooth portion.

In embodiments, the smooth portion may be generally planar. In certain embodiments, the smooth portion may generally define a curved surface. In certain embodiments, the smooth portion may generally define a curved surface of a cylinder.

In embodiments, the generally smooth portion may have a minimum radius of curvature that is larger than the minimum radius of curvature of the shaped elements. The plurality of shaped elements may protrude outwardly from the generally smooth portion.

In embodiments, each (or at least some) of the shaped elements is configured such that an electric field strength around the shaped element is stronger than the electric field strength in surrounding areas of the screen surface, such as the surrounding smooth portion of the screen surface.

In embodiments, each (or at least some) of the shaped elements defines a pointed region. In optional embodiments, the pointed region is the region of the shaped element which is furthest inside the corona discharge zone. In other words, the shaped elements may be configured so as to form pointed regions towards the first electrode. The pointed regions may form protrusions with varying shapes. For example, the pointed regions may form a vertex (or a peak) or a crest.

In embodiments, the peak of the pointed area is of about $10^2$ micro meter order of magnitude.

In embodiments, each (or at least some) of the shaped elements are configured/shaped to ionize air.

In embodiments, each (or at least some) of the shaped elements defines a smooth region (i.e. free of pointed regions). In optional embodiments, the smooth region is the region of the shaped element which is furthest inside the corona discharge zone.

In embodiments, the entirety of each (or at least some) of the shaped elements defines the smooth region. In certain embodiments, each (or at least some) of the shaped elements does not comprise a pointed/sharp region.

In embodiments, each (or at least some) of the shaped elements are configured/shaped to not ionize air.

In embodiments, the screen comprises a first screen element and a second screen element, the second screen element being further inside the corona discharge zone than the first screen element. The first screen element is generally planar. The second screen element defines the plurality of shaped elements. In other words, the screen may be formed of two contiguous screen layers at the same voltages.

In embodiments, the first screen element is spaced apart from the second screen element. In embodiments, the first screen element is electrically insulated from the second screen element. In embodiments, the first screen element and the second screen element are held at different voltages.

In embodiments, the screen surface further defines a flat area which is generally planar. The plurality of shaped elements each protrude from the flat area.

In embodiments, each (or at least some) of the shaped elements protrude from the flat area by a height of between approximately 0.5 mm to approximately 10 mm. Optionally, between approximately 3 mm to approximately 8 mm. Further optionally, between approximately 4 mm to approximately 7 mm.

In embodiments, each (or at least some) of the shaped elements protrude from the flat area by a height of between approximately $1/10^{th}$ to approximately $1/15^{th}$ of the distance between the screen and the second electrode.

In embodiments, the screen surface further defines a flat area which is generally planar. Each (or at least some) of the shaped elements is recessed in the flat area.

In embodiments, each (or at least some) of the shaped elements is recessed in the flat area by a depth of between approximately 1 mm to approximately 10 mm. Optionally, between approximately 3 mm to approximately 8 mm. Optionally, between approximately 4 mm to approximately 7 mm.

In embodiments, each (or at least some) of the shaped elements are spaced apart from each other.

In embodiments, the shaped elements defines a repeating pattern or a combination of repeating elements.

In embodiments, the second electrode is a wire suspended in the hollow housing between the air inlet and the air outlet.

In embodiments, the second electrode is a needle in the hollow housing between the air inlet and the air outlet.

In embodiments, the second electrode is a geometric shape structure with sharp enough edges, or multiple sharp peaks on with small enough surface to create discharge or plasma current.

In another aspect, there is provided an air treatment method. The method comprises conveying an airflow between an air inlet and an opposite air outlet, determining an airflow direction. The method comprises creating a corona discharge zone across the airflow between a screen forming a first electrode and a second electrode, the screen defining a screen surface. The method comprises disrupting dust accumulation on the screen surface using one ore a plurality of shaped elements defined by the screen surface.

In embodiments, each (or at least some) of the shaped elements at least partially shelters a respective downstream side portion of the screen surface from the airflow.

In embodiments, the electric field strength around each of the shaped elements is stronger than the electric field strength in other areas of the screen surface.

In embodiments, more dust accumulates on the shaped elements than other areas of the screen surface.

In embodiments, the second electrode ionizes the airflow.

In embodiments, the screen ionizes the airflow to a lesser extent than the second electrode.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

A general working principle of the air treatment apparatus disclosed herein is converting humidity, present in air, to hydroxyls and hydrogen peroxide ($H_2O_2$), by the influence of discharge current or plasma. The hydrogen peroxide is released from the device to longer distances into the treated airspace with the airflow and may act as a potent biocide, thereby disinfecting the airspace where an apparatus outlet is directed to, an airflow flowing through the air treatment apparatus and the space close to the device in absence of airflow.

As used in the present disclosure, the term "each" may not be exclusively understood as referring to each and every, and when technically relevant may also refer to "at least some".

Figure 1:
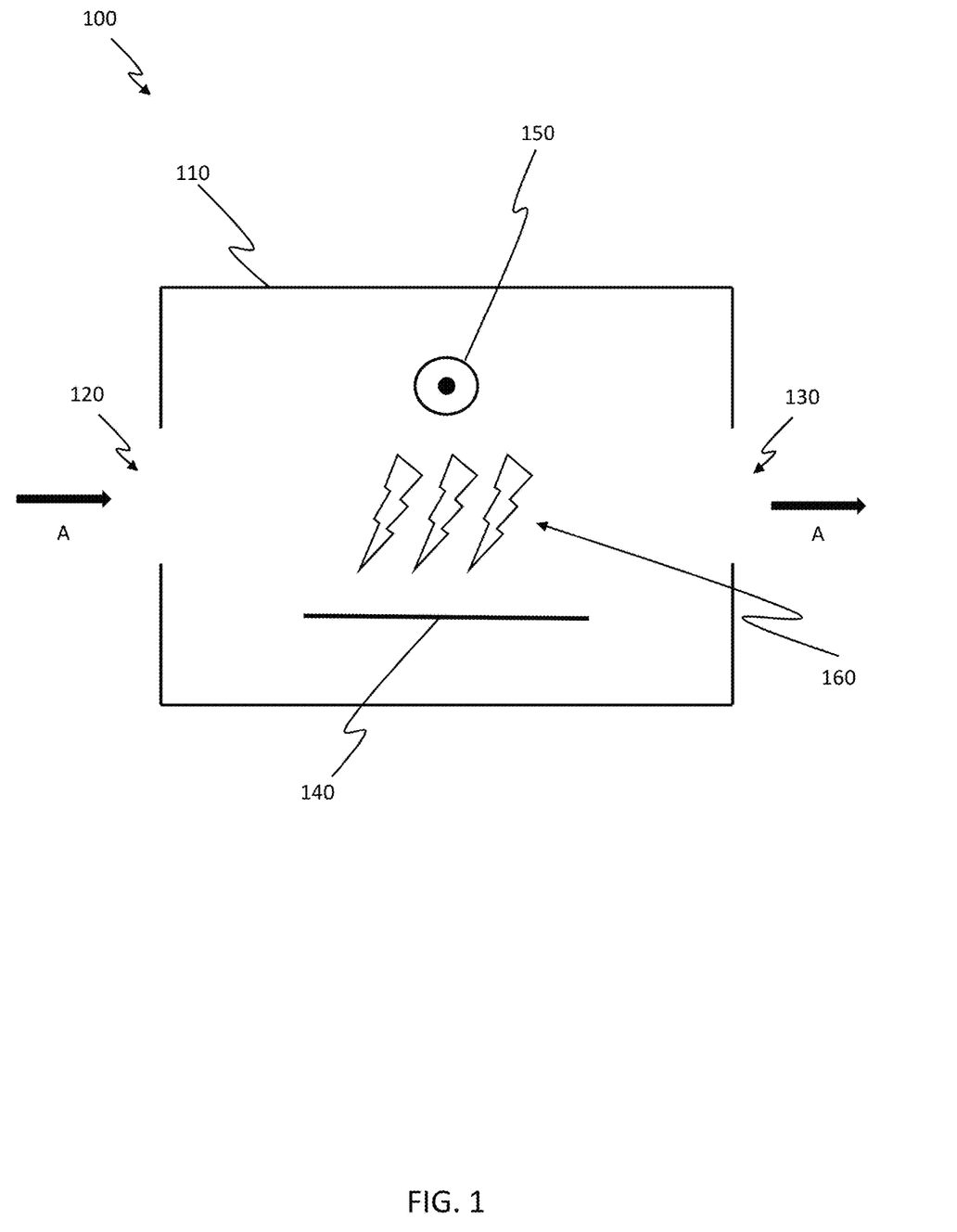
FIG. 1 is a schematic diagram showing a side view of an air treatment apparatus.
Figure 2:
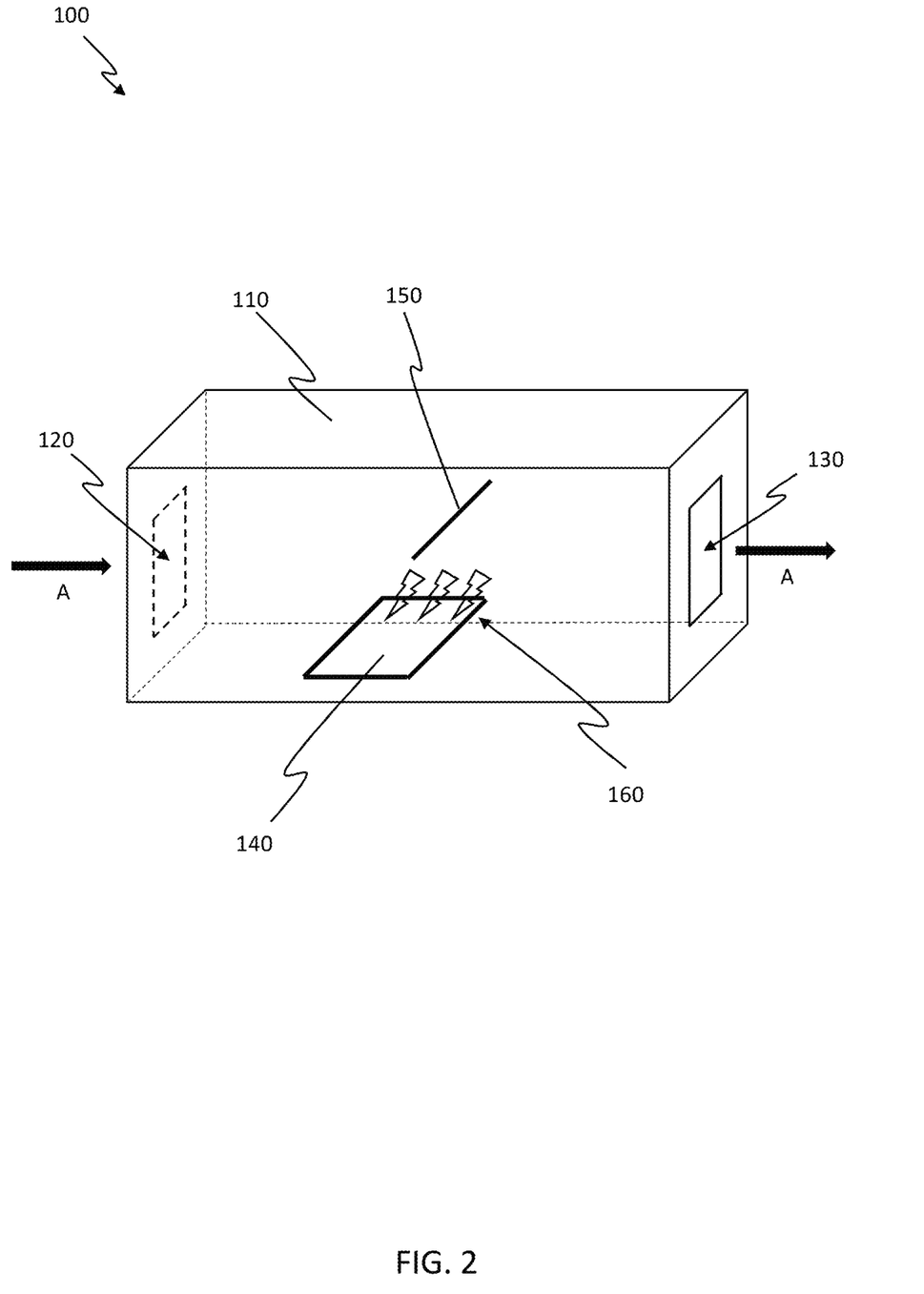
FIG. 2 is a schematic diagram showing a perspective view of the air treatment apparatus of FIG. 1.

FIG. 1 is a schematic diagram showing a side view of an air treatment apparatus 100. FIG. 2 shows a perspective view of the air treatment apparatus 100. The air treatment apparatus 100 may include a housing 110 for conveying an airflow A therethrough. The housing 100 may be hollow. The housing 110 may serve as a casing for containing and/or mounting the components of the air treatment apparatus 10. The housing 110 may also serve a safety purpose of preventing high-voltage electrical components from being accidentally accessed, for example, it may be configured so that a standard human hand cannot access said high-voltage electrical components.

The air treatment apparatus 100 may include an air inlet 120 and may include an air outlet 130. The air inlet 120 and/or the air outlet 130 may be defined in the housing 110, e.g., as respective holes in the housing 110. The air inlet 120 may provide an input for an airflow A to the air treatment apparatus 100. The air outlet 130 may provide an output for a treated airflow A from the air treatment apparatus 100. The air inlet 120 and the air outlet 130 may be disposed generally on opposite sides of the housing 110. The airflow A generally flows in the direction of the arrow shown in FIGS. 1 and 2. In some embodiments, the air treatment apparatus 100 may include attachment means configured for attaching the air treatment apparatus 100 to a source of airflow A such as an air conditioning (A/C) system or fan. In some embodiments, the air treatment apparatus 100 may be configured for attachment to pipes, ducts, and the like, so as to convey the treated airflow A into a target area. For example, in some embodiments, the air treatment apparatus 100 may be incorporated to a ducted air conditioning (A/C) or fan system. In some embodiments, the air inlet 120 of the air treatment apparatus 100 may fluidly communicate with a fan supplying an airflow A, and the air outlet 130 may fluidly communicate with a duct that passes the treated airflow A to a room. For example, the air treatment apparatus 100 may be installed in the return air side or in the air supply outlet of the air conditioner (A/C) ductwork, or in the indoor unit between the filter and coil (e.g., in split air-conditioning systems) or in the air supply inlet.

In some embodiments, the air treatment apparatus 100 may be configured for reversible use i.e., the air outlet 130 may be used as air inlet to the apparatus. The interchangeability between the air inlet 120 and the air outlet 130 means that the air inlet 120 may be used for outlet of air from the air treatment apparatus 100 and the air outlet 130 may be used for inlet of air to the air treatment apparatus 100. In other words, for example, in embodiments where the air treatment apparatus 100 may be installed in an air conditioning (A/C) system, the air treatment apparatus 100 may be installed in a manner such that the air outlet 130 may face the air conditioning airflow output, and the air inlet 120 may face the air conditioning airflow output. In yet other words, there may be no functional distinction between the air inlet 120 and the air outlet 130. The distinction between the air inlet and the air outlet may depend not on any feature of the air treatment apparatus 100, but may depend on any feature, object, or entity that is external to the air treatment apparatus 100.

The air treatment apparatus 100 may include a first electrode 140 and a second electrode 150. The first electrode 140 is in the form of a screen, shown in side profile in FIG. 1. The second electrode 150 is in the form of a wire. Both the screen 140 and the wire 150 are mounted inside the housing 110. The screen 140 and the wire 150 may be mounted between the air inlet 120 and the air outlet 130. In certain embodiments, as shown in FIG. 1, the screen 140 may extend both upstream and downstream relative to the wire 150.

As shown in FIG. 2, the wire 150 may be disposed generally perpendicular to the direction of airflow A. The wire 150 may extend along a wire axis. In some embodiments, the wire axis may be generally aligned with a longitudinal axis of the screen 140. In some embodiments, the wire 150 may be twisted to have the shape of a coil, the shape of a helix, or have a serpentine shape. In some embodiments, the wire 150 may be placed in parallel to the screen 140. In some embodiments, the wire 150 may be sloped/inclined relative to the screen 140. In some embodiments the electrode 150 may be a needle or any object with sharp enough edges to create ionization and corona discharge current.

The screen 140 may include a first electrical terminal (not shown) and the wire 150 may include a second electrical terminal (not shown). The first and second terminals may be electrically connected to the screen 140 and wire 150 for coupling to high and low voltage outputs of a high voltage generator (not shown), whereby a corona discharge zone 160 may be created across the airflow A between the screen 140 and the wire 150. In some embodiments, the high voltage generator may be a unipolar high voltage generator. In some embodiments, the high voltage generator may be a bipolar high voltage generator. In some embodiments, the high voltage generator may be a bipolar high voltage generator operated in switchable mode. For instance, in case of positive corona discharge, the wire 150 may be under +3 kV voltage and the screen(s) 140 may be under −3 kV voltage. In FIGS. 1 and 2, the screen 140 is negatively charged and the wire 150 is positively charged. However, in any of the arrangements disclosed herein, the charges may be reversed, e.g., such that the screen 140 is positively charged and the wire 150 is negatively charged.

As noted above, in the space between the screen 140 and the wire 150, a corona discharge may occur in a corona discharge zone 160. For example, when a sufficient voltage difference is applied between the screen 140 and the wire 150, a corona discharge may occur in the air between the screen 140 and the wire 150. In certain embodiments, the wire 150 acts as an ionizing electrode, and the screen acts as a non-ionizing electrode, as would be understood by those skilled in the art. In alternative embodiments, the wire 150 acts as a primary ionizing electrode, and the screen (or parts thereof) acts as a secondary ionizing electrode, producing opposite corona discharges (as explained below).

Herein, the first electrode 140 may be referred to as a wire, an ionizing electrode and/or a primary ionizing electrode. The second electrode 150 may be referred to as a screen, a non-ionizing electrode and/or a secondary ionizing electrode.

With the apparatuses disclosed herein, the corona discharge in the corona discharge zone 160 may create ions and may convert humidity, present in air, to hydroxyls and hydrogen peroxide ($H_2O_2$). The hydrogen peroxide may then act as a potent biocide, thereby disinfecting the air, while hydroxyls can treat the air close to the apparatus. The combination of the screen 140 and wire 150 acting as electrodes to cause the corona discharge in the corona discharge zone 160 may also produce ions which also act to treat the air, for example, by also acting as potent bioaerosols purifiers. In the case of the embodiment of FIGS. 1 and 2, the wire 150 is positively charged and is configured to act as an ionizing electrode. Air passing close to (or hitting) the wire 150 is ionized and forms positive ions. The positive ions may then be attracted to the screen 140 which is negatively charged. This causes a build up of dust particles on the surface of the screen 140 (as described below).

Figure 3:
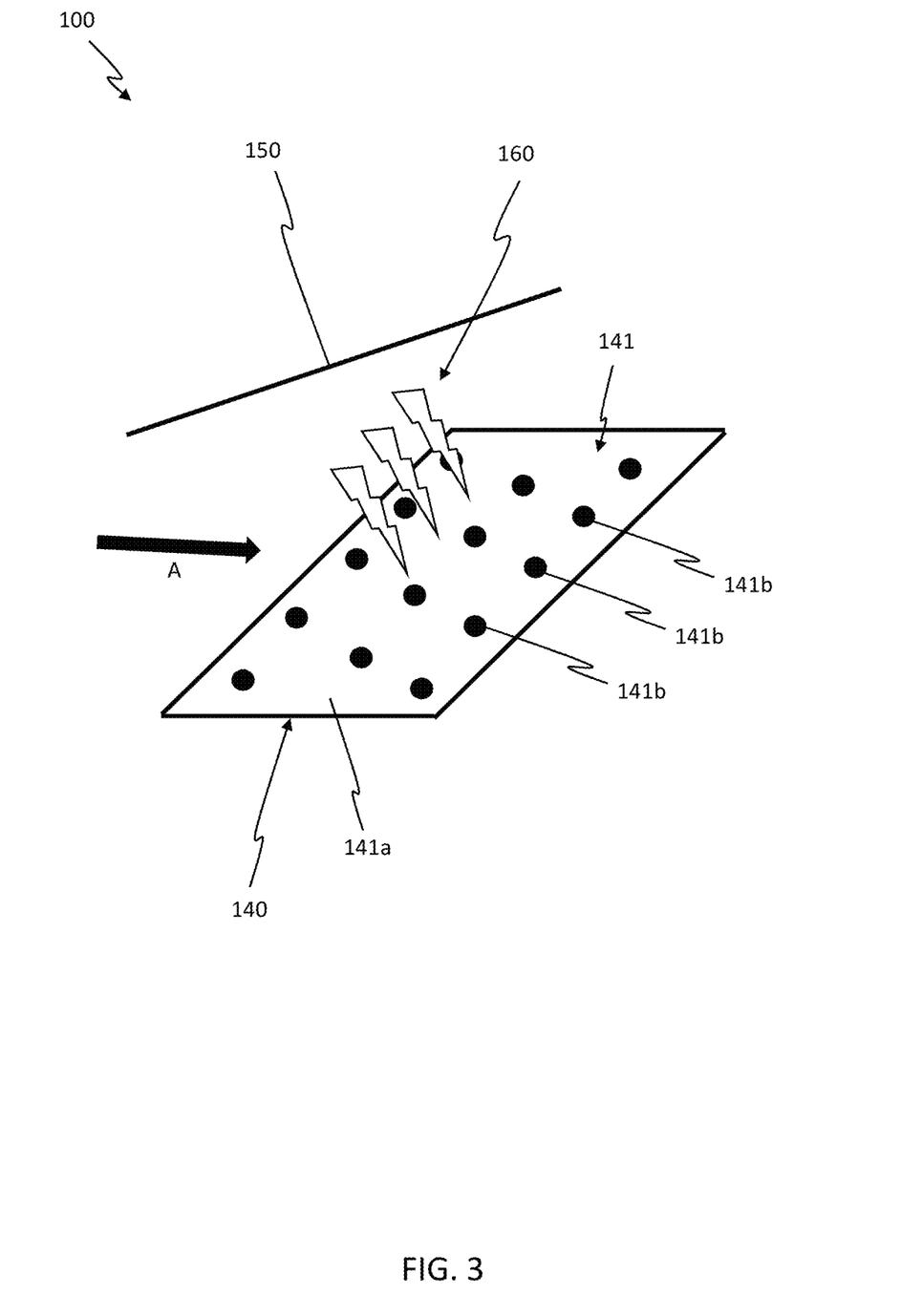
FIG. 3 shows a view of a screen, a wire and a corona discharge zone of the air treatment apparatus of FIG. 1.

FIG. 3 shows a close view of the screen 140, the wire 150 and the corona discharge zone 160 created therebetween. Other elements of the air treatment apparatus 100 are hidden for clarity.

The screen 140 defines a screen surface 141. The screen surface 141 is exposed to the corona discharge zone 160. Accordingly, airflow A may flow over the screen surface 141. The screen surface 141 may be the surface of the screen 140 which faces the wire 150. The screen surface 141 may be the surface of the screen 140 which is most exposed to the corona discharge zone 160. Positive ions created by the wire 150 acting as an ionizing electrode are attracted to the screen 140, and, in particular, the screen surface 141. Dust (e.g. from the positive ions) may gather on the screen surface 141 over time and form a layer thereon.

The screen surface 141 may define a generally smooth surface 141a and a plurality of shaped elements 141b. FIG. 3 merely shows a representation of the plurality of shaped elements 141b and further specific embodiments are provided below. The smooth surface 141a and the plurality of shaped elements 141b are exposed to the corona discharge zone 160. Accordingly, airflow A may flow over the screen surface 141, and, in particular, the smooth surface 141a and the plurality of shaped elements 141b. In certain embodiments (e.g. that shown in FIG. 3), the smooth surface 141a may be generally planar or generally flat. In other embodiments, the smooth surface 141a may be in the shape of (part of) the surface of a cylinder or other curved surface. In certain embodiments, the smooth surface 141a may form the majority of the surface area of the screen surface 141. In certain embodiments, the plurality of shaped elements 141b may form the minority of the surface area of the screen surface 141.

The plurality of shaped elements 141b may be arranged in a repeating pattern (as shown in FIG. 3), or a combination of repeating elements. In other embodiments, the plurality of shaped elements 141b may be positioned randomly on the screen surface 141.

Generally, the shaped elements 141b are each configured to disrupt dust accumulation on the screen surface 141. Disruption of dust accumulation on the screen surface 141 may be achieved by several physical means.

For example, the shaped elements 141b may each be configured to disrupt dust accumulation on the screen surface 141 by stimulating uneven dust accumulation on the screen surface 141 (as opposed to an entirely smooth screen which results in a uniform layer of dust). As used herein, uneven dust accumulation may refer to dust being accumulated on the screen surface 141 in differing amounts/by differing speeds depending on the specific location on the screen surface 141 (e.g. depending on the proximity of any one of the plurality of shaped elements 141b). In certain embodiments, uneven dust accumulation on the screen surface 141 may form in a pattern which generally corresponds to the pattern of the plurality of shaped elements 141b. Configurations of the screen 140 which may result in uneven dust accumulation are detailed below.

In another example, the shaped elements 141b may each be configured to disrupt dust accumulation on the screen surface 141 by reducing the total amount of dust that accumulates on the screen surface 141. Configurations of the screen 140 which may result in uneven dust accumulation are detailed below.

In certain examples, the shaped elements 141b may each be configured to disrupt dust accumulation on the screen surface 141 by both: i) stimulating uneven dust accumulation on the screen surface 141; and ii) reducing the amount of dust that accumulates on the screen surface 141.

Figure 4A:
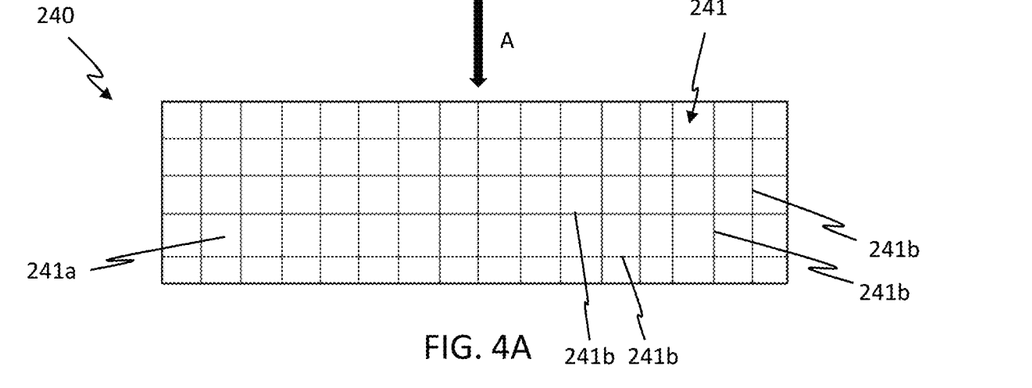
FIGS. 4A to 4C show an exemplary screen of the air treatment apparatus of FIG. 1.
Figure 4B:
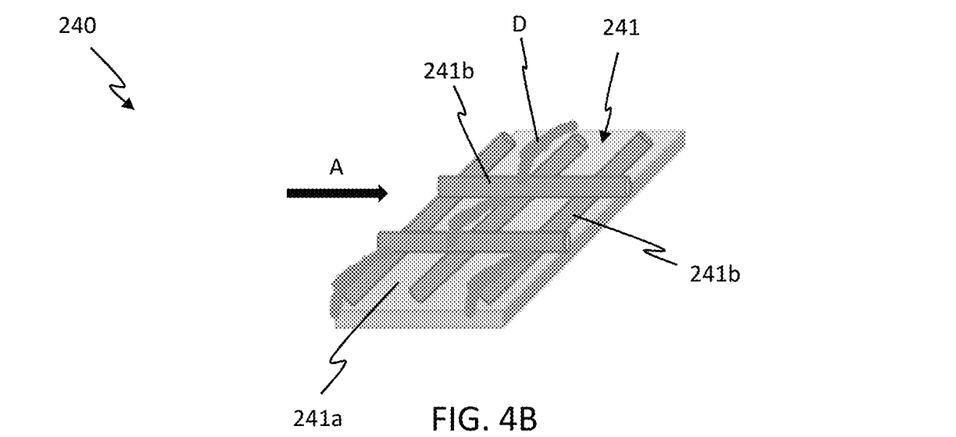
Figure 4C:
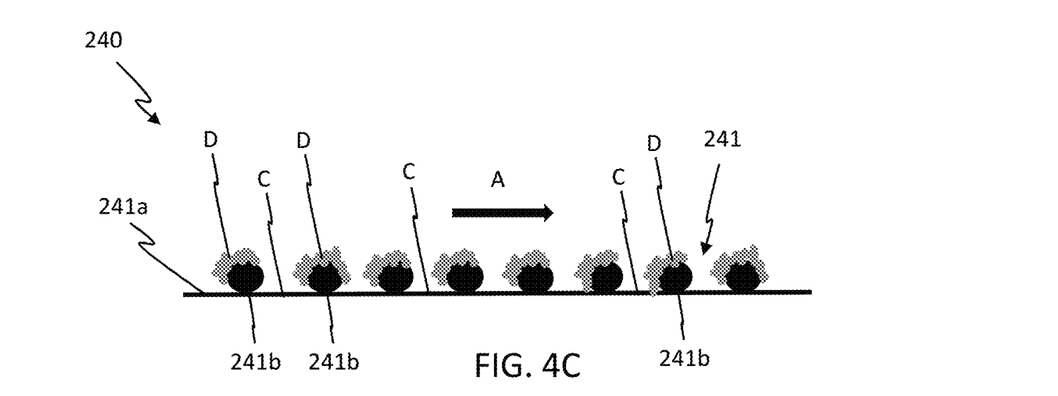

FIGS. 4A to 4C show an exemplary screen 240. The screen 240 defines a screen surface 241 which is exposed to the corona discharge zone 160 (not marked in FIGS. 4A to 4C). Airflow A may flow over the screen surface 241 in the direction shown by the arrows.

The screen surface 241 defines a generally smooth surface 241a. The smooth surface 241a is generally planar. The smooth surface 241a forms the majority of the surface area of the screen surface 241.

The screen surface 241 also defines a plurality of shaped elements 241b. Each of the plurality of shaped elements 241b is generally in the shape of a wire (e.g. of a circular cross section). The plurality of shaped elements 241b are arranged to together define a grid. The grid may comprise a set of the plurality of shaped elements 241b which generally align with the direction of the airflow A and another set of the plurality of shaped elements 241b which are generally perpendicular to the direction of the airflow A. The grid may comprise of a set of the plurality of shaped elements 241b forming a rectangular, square or rhombic pattern, aligned to the airflow A from various sides of the geometric structures formed.

The plurality of shaped elements 241b protrude from the smooth surface 241a. In other words, the plurality of shaped elements 241b defines a grid which protrudes from the smooth surface 241a. The shaped elements 241b and/or the grid protrudes from the smooth surface 241a such that it is further inside the corona discharge zone 160 (not marked in FIGS. 4A to 4C) than the smooth surface 241a.

Generally, each of the plurality of shaped elements 241b may be configured/shaped such that they do not act as an ionizing electrode (i.e. a non-ionizing electrode). In such configurations, the screen 240 acts as a non-ionizing electrode.

In the embodiment of FIGS. 4A to 4C, at least some of (or all of) the plurality of shaped elements 241b forming the grid are touching the smooth surface 241a. In such embodiments, the smooth surface 241a and the plurality of shaped elements 241b are held at the same voltage. In alternative embodiments, at least some of (or all of) the plurality of shaped elements 241b forming the grid are spaced apart/not touching/electrically insulated from the smooth surface 241a. In such embodiments, the smooth surface 241a and the plurality of shaped elements 241b may be held at differing voltages (as explained in further detail below). In alternative embodiments, at least some of (or all of) the plurality of shaped elements 241b forming the grid are spaced apart and element 241a is absent.

As shown specifically in FIGS. 4B and 4C, dust D gathers on the screen surface 241. Due to the plurality of shaped elements 241b, the dust D accumulates unevenly on the screen surface 241 (i.e. the plurality of shaped elements 241b disrupt the dust accumulation). The plurality of shaped elements 241b (and in particular, those which are aligned generally perpendicular to the airflow direction) act to at least partially shelter a respective downstream side portion of the screen surface 241 from the airflow. This may create portions of the screen surface 241 which generally deposited with less dust D (clean portions C of the screen surface 241). The plurality of shaped elements 241b (and in particular, those which are aligned generally perpendicular to the airflow direction) may therefore be deposited with more dust D, thereby creating uneven dust accumulation on the screen surface 241. This may result in great efficacy of the apparatus as the working life of the screen 240 is increased as areas of the screen surface 241 are exposed (i.e. not fully covered with dust D) for longer.

Figure 5A:
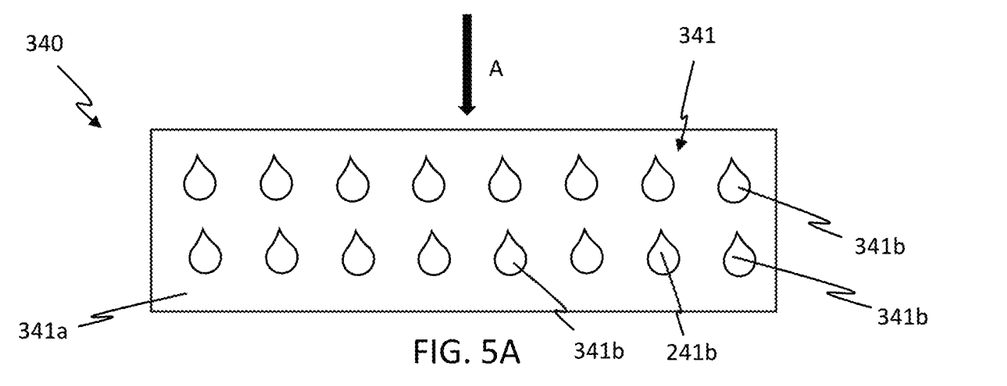
FIGS. 5A to 5C show another exemplary screen of the air treatment apparatus of FIG. 1.
Figure 5B:
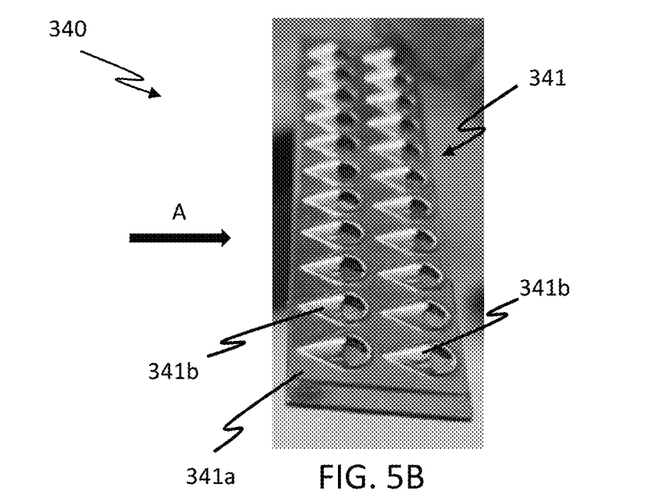
Figure 5C:
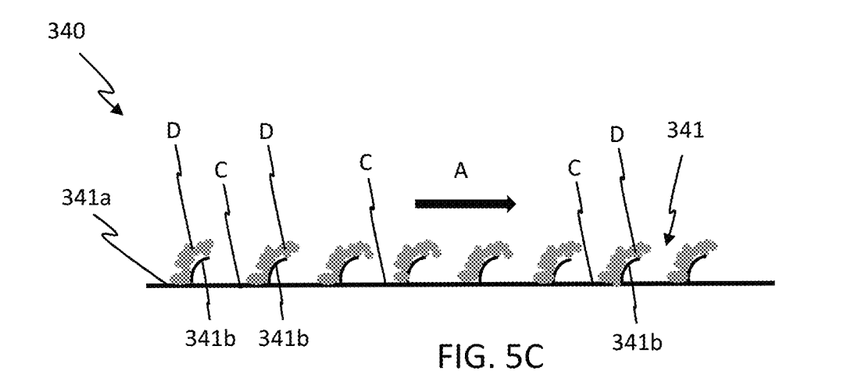

FIGS. 5A to 5C show another exemplary screen 340. The screen 340 defines a screen surface 341 which is exposed to the corona discharge zone 160 (not marked in FIGS. 5A to 5C). Airflow A may flow over the screen surface 341 in the direction shown by the arrows.

The screen surface 341 defines a generally smooth surface 341a. The smooth surface 341a is generally planar. The smooth surface 341a forms the majority of the surface area of the screen surface 341.

The screen surface 341 also defines a plurality of shaped elements 341b. Each of the plurality of shaped elements 341b is generally in the shape of a section of a curved cone surface. The plurality of shaped elements 341b are arranged in a repeating pattern. The plurality of shaped elements 341b are generally aligned in a direction generally parallel to the airflow direction and generally aligned in a direction generally perpendicular to the airflow direction.

The plurality of shaped elements 341b each protrude from the smooth surface 341a. The shaped elements 341b each protrude from the smooth surface 341a such that they are each further inside the corona discharge zone 160 (not marked in FIGS. 5A to 5C) than the smooth surface 341a.

As can be seen most clearly in FIG. 5B, each of the plurality of shaped elements 341b define a smooth/continuous surface region. The smooth/continuous region may be the entirety of the surface of the respective shaped element 341b and/or the smooth/continuous region may be the region of the respective shaped element 341b which is furthest inside the corona discharge zone 160 (not marked in FIGS.

5A to 5C). In other words, in certain embodiments, the surfaces of each of the plurality of shaped elements 341b do not define any sharp points/elements.

Generally, each of the plurality of shaped elements 341b may be configured/shaped such that they do not act as an ionizing electrode (i.e. a non-ionizing electrode). In such configurations, the screen 340 acts as a non-ionizing electrode.

In the embodiment of FIGS. 5A to 5C, each of the plurality of shaped elements 241b define a hole in the screen 340 (and the screen surface 341). However, in alternative embodiments, these holes may be omitted (e.g. the inner parts of the each of the plurality of shaped elements 341b being closed with the screen 340 material. In such embodiments, the screen 340 (and the screen surface 341) does not define any holes. In certain embodiments, the screen 340 further comprises a second (continuous) layer disposed below the plurality of shaped elements 341b.

In the embodiment of FIGS. 5A to 5C, at least some of (or all of) the plurality of shaped elements 341b are touching the smooth surface 341a (in the case of the embodiment of FIGS. 5A to 5C, the plurality of shaped elements 341b and the smooth surface 341a are integral/continuous). In such embodiments, the smooth surface 341a and the plurality of shaped elements 341b are held at the same voltage. In alternative embodiments, at least some of (or all of) the plurality of shaped elements 341b are spaced apart/not touching/electrically insulated from the smooth surface 341a. In such embodiments, the smooth surface 341a and the plurality of shaped elements 341b may be held at differing voltages (as explained in further detail below).

As shown specifically in FIG. 5C, dust D gathers on the screen surface 341. Due to the plurality of shaped elements 341b, the dust D accumulates unevenly on the screen surface 341 (i.e. the plurality of shaped elements 341b disrupt the dust accumulation). The plurality of shaped elements 341b act to at least partially shelter a respective downstream side portion of the screen surface 341 from the airflow. Furthermore, as the plurality of shaped elements 341b extend further into the corona discharge zone 160 (not marked in FIGS. 5A to 5C) than the smooth surface 341a, each of the plurality of shaped elements 341b are surround by a stronger electric field than the surrounding smooth surface 341a. This stronger electric field which surrounds each of the plurality of shaped elements 341b more strongly attracts dust D and therefore is generally deposited with more dust D. Both these factors (sheltering and creating a stronger electric field) may create portions of the screen surface 341 which are generally deposited with less dust D (clean portions C of the screen surface 341). The plurality of shaped elements 341b may therefore be deposited with more dust D, thereby creating uneven dust accumulation on the screen surface 341. This may result in great efficacy of the apparatus as the working life of the screen 340 is increased as areas of the screen surface 341 are exposed (i.e. not fully covered with dust D) for longer.

Figure 6A:
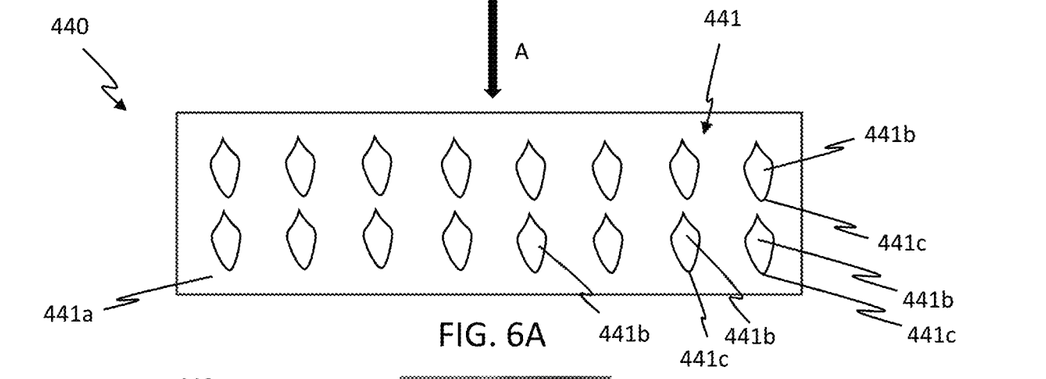
FIGS. 6A to 6C show a further exemplary screen of the air treatment apparatus of FIG. 1.
Figure 6B:
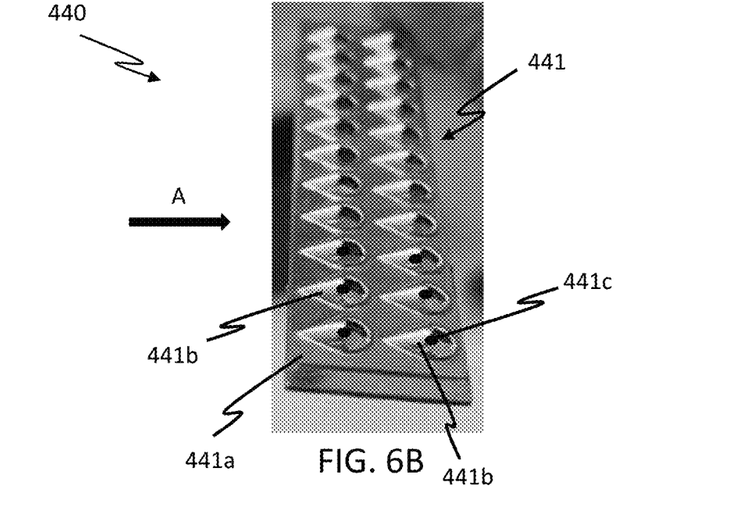
Figure 6C:
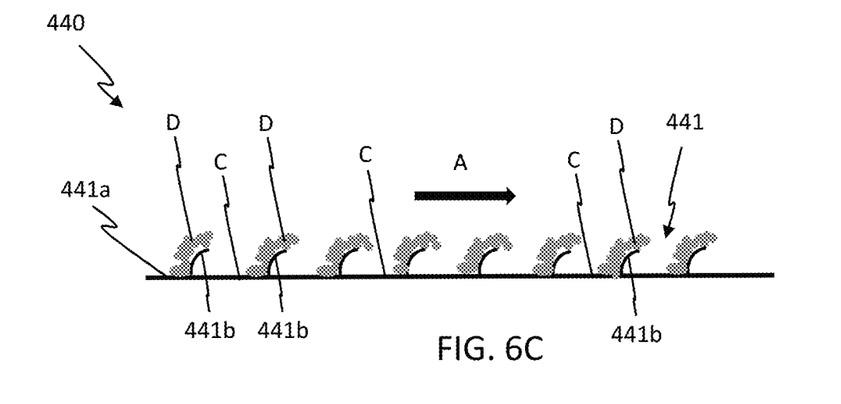

FIGS. 6A to 6C show a further exemplary screen 440. The screen 440 shown in FIGS. 6A to 6C is similar to screen 340 shown in FIGS. 5A to 5C apart from the shape of the most protruding part thereof.

Specifically, the screen 440 defines a screen surface 441 which is exposed to the corona discharge zone 160 (not marked in FIGS. 6A to 6C). Airflow A may flow over the screen surface 441 in the direction shown by the arrows.

The screen surface 441 defines a generally smooth surface 441a. The smooth surface 441a is generally planar. The smooth surface 441a forms the majority of the surface area of the screen surface 441.

The screen surface 441 also defines a plurality of shaped elements 441b. Each of the plurality of shaped elements 441b is generally in the shape of a section of a curved cone surface with the most protruding part thereof forming a sharp point (described further below). The plurality of shaped elements 441b are arranged in a repeating pattern. The plurality of shaped elements 441b are generally aligned in a direction generally parallel to the airflow direction and generally aligned in a direction generally perpendicular to the airflow direction.

The plurality of shaped elements 441b each protrude from the smooth surface 441a. The shaped elements 441b each protrude from the smooth surface 441a such that they are each further inside the corona discharge zone 160 (not marked in FIGS. 6A to 6C) than the smooth surface 441a.

Each of the plurality of shaped elements 441b defines a pointed region 441c. The pointed region 441c may be the region of the shaped element 341b that is furthest inside the corona discharge zone 160 (not marked in FIGS. 5A to 5C)— in other words, the most protruding part of the shaped element 441b. The rest of the shaped elements 441b may be smooth/continuous.

Generally, each of the plurality of shaped elements 341b may be configured/shaped such that they act to ionize the air (for example, due to the pointed region 441c). In this way, the screen 440 may act as an ionizing electrode. In certain embodiments, the screen 440 may be configured to ionize the air to a lesser extent than the wire 150. In certain embodiments, the screen 440 may ionize air approximately 1% to 10% or more of the extent to which the wire 150 ionizes air. In such configurations, the screen 440 produces oppositely charged ions than the wire 150 (i.e. the screen 440 produces negatively charged ions and the wire 150 produces positively charged ions (dust D)). The negatively charged ions produced by the screen 440 may neutralize the positively charged dust D thereby reducing the attraction of the dust D to the screen 440. In this manner, the amount of dust D which is attracted to the screen 440 (and settles/accumulates on the screen 440) is reduced.

In the embodiment of FIGS. 6A to 6C, each of the plurality of shaped elements 441b define a hole in the screen 440 (and the screen surface 441). However, in alternative embodiments, these holes may be omitted (e.g. the inner parts of the each of the plurality of shaped elements 441b being closed with the screen 440 material. In such embodiments, the screen 440 (and the screen surface 441) does not define any holes. In certain embodiments, the screen 440 further comprises a second (continuous) layer disposed below the plurality of shaped elements 441b.

In the embodiment of FIGS. 6A to 6C, at least some of (or all of) the plurality of shaped elements 441b are touching the smooth surface 441a (in the case of the embodiment of FIGS. 6A to 6C, the plurality of shaped elements 441b and the smooth surface 441a are integral/continuous). In such embodiments, the smooth surface 441a and the plurality of shaped elements 441b are held at the same voltage. In alternative embodiments, at least some of (or all of) the plurality of shaped elements 441b are spaced apart/not touching/electrically insulated from the smooth surface 441a. In such embodiments, the smooth surface 441a and the plurality of shaped elements 441b may be held at differing voltages (as explained in further detail below).

As shown specifically in FIG. 6C, dust D gathers on the screen surface 441. Due to the plurality of shaped elements 341b, the dust D accumulates unevenly on the screen surface 441 and to a lesser extent (i.e. the plurality of shaped elements 441b disrupt the dust accumulation). This may result in great efficacy of the apparatus as the working life of the screen 340 is increased as areas of the screen surface 341 are exposed (i.e. not fully covered with dust D) for longer.

Figure 7A:
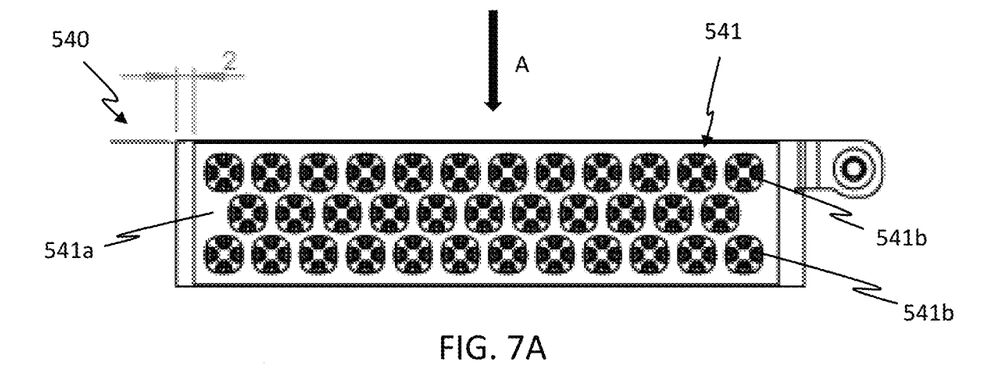
FIGS. 7A to 7C show yet another exemplary screen of the air treatment apparatus of FIG. 1.
Figure 7B:
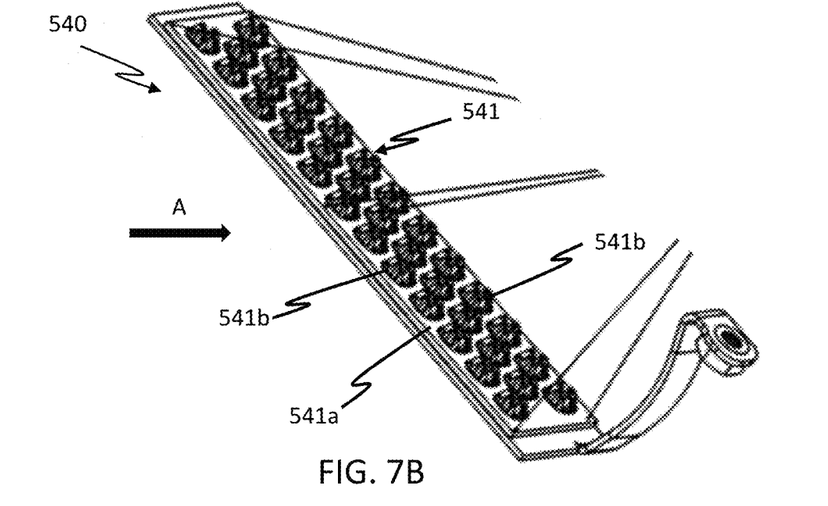
Figure 7C:
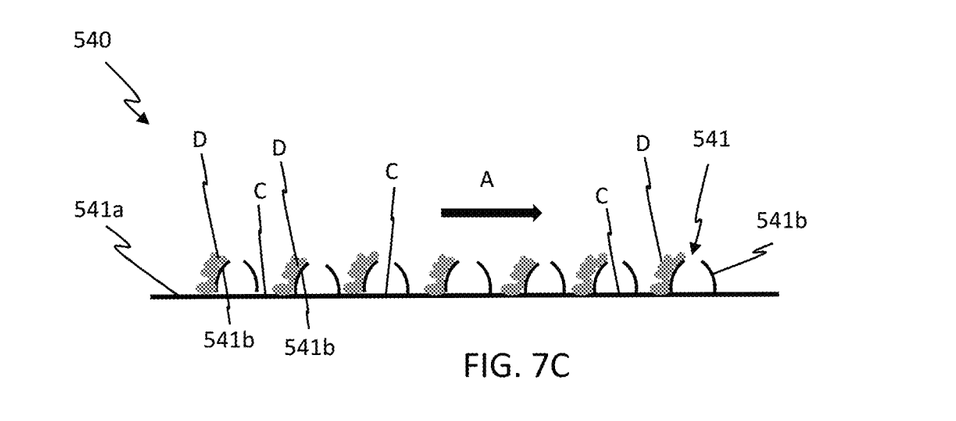

FIGS. 7A to 7C show another exemplary screen 540. The screen 540 defines a screen surface 541 which is exposed to the corona discharge zone 160 (not marked in FIGS. 7A to 7C). Airflow A may flow over the screen surface 541 in the direction shown by the arrows.

The screen surface 541 defines a generally smooth surface 541a. The smooth surface 541a is generally planar. The smooth surface 541a may form the majority of the surface area of the screen surface 541.

The screen surface 541 also defines a plurality of shaped elements 541b. Each of the plurality of shaped elements 541b is generally formed from two or more leaves. In the configuration shown in FIGS. 7A to 7C, each of the plurality of shaped elements 541b is generally formed from four leaves. Each of the leaves protrudes from the generally smooth surface 541a. In certain embodiments, the leaves are not connected to each other (except via the generally smooth surface 541a). In certain embodiments, the leaves may be flat or curved. In some embodiments, the leaves may have a triangular or trapezoid shape. In some embodiments, the leaves may be vertical or tilted towards the screen surface 541. In certain embodiments, the leaves generally correspond to part of the shape of the surface a sphere.

The plurality of shaped elements 541b may be arranged in a repeating pattern. The plurality of shaped elements 541b may be generally offset in a direction generally parallel to the airflow direction and/or generally offset in a direction generally perpendicular to the airflow direction.

The plurality of shaped elements 541b each protrude from the smooth surface 541a. The shaped elements 541b may each protrude from the smooth surface 541a such that they are further inside the corona discharge zone 160 (not marked in FIGS. 7A to 7C) than the smooth surface 541a.

Each of the plurality of shaped elements 541b may define a smooth/continuous surface region. The smooth/continuous region may be the entirety of the surface of the respective shaped element 541b and/or the smooth/continuous region may be the region of the respective shaped element 541b which is furthest inside the corona discharge zone 160 (not marked in FIGS. 7A to 7C). In other words, in certain embodiments, the surfaces of each of the plurality of shaped elements 541b do not define any sharp points/elements. Generally, each of the plurality of shaped elements 541b may be configured/shaped such that they do not act as an ionizing electrode (i.e. a non-ionizing electrode). In such configurations, the screen 540 acts as a non-ionizing electrode.

In alternative embodiments, each of the plurality of shaped elements 541b defines a pointed region. The pointed region may be the region of the shaped element 541b that is furthest inside the corona discharge zone 160 (not marked in FIGS. 7A to 7C)— in other words, the most protruding part of the shaped element 541b. The rest of the shaped elements 541b may be smooth/continuous. Generally, each of the plurality of shaped elements 541b may be configured/shaped such that they act to ionize the air (for example, due to the pointed region). In this way, the screen 540 may act as an ionizing electrode. In certain embodiments, the screen 540 may be configured to ionize the air to a lesser extent than the wire 150. In certain embodiments, the screen 540 may ionize air approximately 1% to 10% or more of the extent to which the wire 150 ionizes air. In such configurations, the screen 540 produces oppositely charged ions than the wire 150 (i.e. the screen 540 produces negatively charged ions and the wire 150 produces positively charged ions (dust D)). The negatively charged ions produced by the screen 540 may neutralize the positively charged dust D thereby reducing the attraction of the dust D to the screen 540. In this manner, the amount of dust D which is attracted to the screen 540 (and settles/accumulates on the screen 540) is reduced.

Each of the plurality of shaped elements 541b may optionally define a hole in the screen 540 (and the screen surface 541). However, in alternative embodiments, these holes may be omitted (e.g. the inner parts of the each of the plurality of shaped elements 541b being closed with the screen 540 material. In such embodiments, the screen 540 (and the screen surface 541) does not define any holes. In certain embodiments, the screen 540 further comprises a second (continuous) layer disposed below the plurality of shaped elements 541b.

In the embodiment of FIGS. 7A to 7C, at least some of (or all of) the plurality of shaped elements 541b are touching the smooth surface 541a (in the case of the embodiment of FIGS. 7A to 7C, the plurality of shaped elements 541b and the smooth surface 541a are integral/continuous). In such embodiments, the smooth surface 541a and the plurality of shaped elements 541b are held at the same voltage. In alternative embodiments, at least some of (or all of) the plurality of shaped elements 541b are spaced apart/not touching/electrically insulated from the smooth surface 541a. In such embodiments, the smooth surface 541a and the plurality of shaped elements 541b may be held at differing voltages (as explained in further detail below).

As shown specifically in FIG. 7C, dust D gathers on the screen surface 541. Due to the plurality of shaped elements 541b, the dust D accumulates unevenly on the screen surface 541 (i.e. the plurality of shaped elements 541b disrupt the dust accumulation). The plurality of shaped elements 541b act to at least partially shelter a respective downstream side portion of the screen surface 541 from the airflow. Furthermore, as the plurality of shaped elements 541b extend further into the corona discharge zone 160 (not marked in FIGS. 7A to 7C) than the smooth surface 541a, each of the plurality of shaped elements 541b are surround by a stronger electric field than the surrounding smooth surface 541a. This stronger electric field which surrounds each of the plurality of shaped elements 541b more strongly attracts dust D and therefore is generally deposited with more dust D. Both these factors (sheltering and creating a stronger electric field) may create portions of the screen surface 541 which are generally deposited with less dust D (clean portions C of the screen surface 541). The plurality of shaped elements 541b may therefore be deposited with more dust D, thereby creating uneven dust accumulation on the screen surface 541. This may result in great efficacy of the apparatus as the working life of the screen 540 is increased as areas of the screen surface 541 are exposed (i.e. not fully covered with dust D) for longer.

In some embodiments the shaped element is single per electrode, in some embodiments the shaped elements are plural on each electrode, in some embodiments the shaped elements are the same and may form the pattern, in some embodiments there is a combination of different shaped elements on the electrode surface.

In the embodiments described above, the entirety of the screen 140, 240, 340, 440, 540 is held at the same voltage. However, if areas of the screen 140, 240, 340, 440, 540 is electrically separated from other areas of the screen 140, 240, 340, 440, 540 these two different areas can be held at different voltages (as noted above). The difference in voltages may be used to further manipulate the dust accumulation on the screen 140, 240, 340, 440, 540. For example, in any of the embodiments described herein, the shaped elements may be held at a different voltage to the smooth surface of the screen.

A method of treating air is now described. The method may use any of the air treatment apparatuses disclosed herein.

The air to be treated is conveyed through the air inlet 120 of the air treatment device 100. A corona discharge in the corona discharge zone 160 is created across the airflow A between the screen 140, 240, 340, 440, 540 acting as a first electrode and a wire 150 acting as a second electrode. The corona discharge is created by applying a sufficiently high voltage difference between the screen 140, 240, 340, 440, 540 and the wire 150. Ions are formed due to the corona discharge which may treat the air, for example, by acting to remove floating pathogens. The screen 140, 240, 340, 440, 540 may include a plurality of shaped elements 141b, 241b, 341b, 441b, 541b which act to disrupt dust accumulation on the screen 140, 240, 340, 440, 540.

The dust accumulation on the screen 140, 240, 340, 440, 540 may be disrupted by both: i) stimulating uneven dust accumulation on the screen surface 141, 241, 341, 441, 541; and ii) reducing the amount of dust that accumulates on the screen surface 141, 241, 341, 441, 541 (as described above).

While at least one exemplary embodiment has been presented in the foregoing detailed description, it should be appreciated that a vast number of variations exist.

For example, in the above exemplary embodiments, the air treatment apparatus 100 comprises a single screen 140, 240, 340, 440, 540. However, any number of screens may be used. For example, another screen (similar to screen 140, 240, 340, 440, 540) may be included on the other side of the wire 150 (symmetrically to the first screen 140, 240, 340, 440, 540).

Furthermore, in the above exemplary embodiments, the air treatment apparatus 100 comprises a wire 150 as the second electrode. The wire 150 acts to ionize the airflow A. However, in alternative embodiments, the wire 150 may be replaced by a needle acting as the second electrode. The needle may act to ionize the airflow A. In other embodiments the wire 150 can be removed on any object with sharp edges, like screw, multi-needle rod, rod with sharp edges.

The screen 140, 240, 340, 440, 540 is shown as being generally planar/flat with shaped elements in the above embodiments. However, in alternative embodiments, the screen may take a curved shape (such as cylindrical) with the shaped elements disposed thereon. In other words, the smooth surface described herein does not necessarily need to be generally flat, but instead may curve itself. As would be understood by those skilled in the art, the term 'smooth' relates to the relative shapes of the smooth/flat surface and the shaped elements. For example, the smooth surface is generally smoother than the shaped elements. The smooth surface may have a minimum radius of curvature that is larger than the minimum radius of curvature of the shaped elements.

As would be understood by the skilled person, the shapes and arrangements of the plurality of shaped elements shown in FIGS. 4 to 7 are exemplary in nature. The specific forms may be changed to modify the particular dust accumulation amount and pattern.

It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the disclosure as set forth in the appended claims and the legal equivalents thereof.

The invention claimed is:

1. An air treatment apparatus, comprising:
    (a) a hollow housing for conveying an airflow between an air inlet and an opposite air outlet, determining an airflow direction;
    (b) a screen forming a first electrode, the screen being mounted in the housing between the air inlet and the air outlet and defining a generally planar screen surface; and
    (c) a second electrode, wherein:
        i) the air treatment apparatus is configured to apply a voltage across the first electrode and the second electrode such that a corona discharge zone is formed across the airflow between the screen and the second electrode; and
        ii) the screen surface is exposed to the corona discharge zone and hosts one or more shaped elements extending from said screen surface into said corona discharge zone across said airflow thereby inhibiting dust accumulation downstream of said one of more shaped elements on the screen surface.

2. The air treatment apparatus of claim 1, wherein each of the one or more shaped elements is configured to at least partially shelter a respective downstream side portion of the screen surface from the airflow.

3. The air treatment apparatus of claim 2, wherein said one or more shaped elements extend over a portion of said screen thereby sheltering a portion of said screen disposed between said shaped element and said corona discharge zone.

4. The air treatment apparatus of claim 3, wherein said one or more shaped elements extend over said portion of said screen in a direction including a component parallel to said generally planar surface.

5. The air treatment apparatus of claim 1, wherein each of the one or more shaped elements is configured such that an electric field strength around the shaped element is stronger than the electric field strength in other areas of the screen surface.

6. The air treatment apparatus of claim 1, wherein each of the one or more shaped elements defines a pointed region, optionally, the pointed region is the region of the shaped element which is furthest inside the corona discharge zone.

7. The air treatment apparatus of claim 1, wherein each of the one or more shaped elements defines a smooth region, optionally, the smooth region is the region of the shaped element which is furthest inside the corona discharge zone.

8. The air treatment apparatus of claim 1, wherein the screen comprises a first screen element and a second screen element, the second screen element being further inside the corona discharge zone than the first screen element, wherein the first screen element is generally planar, and wherein the second screen element defines the one or more shaped elements.

9. The air treatment apparatus of claim 1, wherein said generally planar screen surface defines a flat area;
   wherein each of the one or more shaped elements protrude from the flat area by a height of between approximately 0.5 mm to approximately 10 mm, optionally, between approximately 3 mm to approximately 8 mm, and further optionally, between approximately 4 mm to approximately 7 mm.

10. The air treatment apparatus of claim 1, wherein said generally planar screen surface defines a flat area, the apparatus comprising one or more shaped elements recessed in the flat area.

11. The air treatment apparatus of claim 10, wherein each of the one or more shaped elements recessed in the flat area are recessed by a depth of between approximately 1 mm to approximately 10 mm, optionally, between approximately 3 mm to approximately 8 mm, and further optionally, between approximately 4 mm to approximately 7 mm.

12. The air treatment apparatus of claim 1, wherein each of the one or more shaped elements are spaced apart from each other.

13. The air treatment apparatus of claim 1, wherein the one or more shaped elements defines a repeating pattern or a combination of the same or different shaped repeating elements.

14. The air treatment apparatus of claim 1, wherein the second electrode is a wire suspended in the hollow housing between the air inlet and the air outlet.

15. The air treatment apparatus of claim 1, wherein the second electrode is a needle in the hollow housing between the air inlet and the air outlet.

16. The air treatment apparatus of claim 1, wherein said one or more shaped elements have a leading edge extending into said corona discharge zone across said airflow at an angle towards said airflow.

17. The air treatment apparatus of claim 1, wherein said screen surface is a continuous surface.

18. The air treatment apparatus of claim 1, comprising a voltage generator configured to provide a voltage between said first electrode and said second electrode of under 6 kV.

19. The air treatment apparatus of claim 1, wherein said generally planar surface forms a majority of a surface area of said screen surface and said one or more shaped element form a minority of said surface are of said screen surface.

* * * * *